US011826310B2

United States Patent
Matharu (10) Patent No.: US 11,826,310 B2
(45) Date of Patent: Nov. 28, 2023

(54) PORTABLE APPARATUS AND METHOD FOR STERILE PHARMACEUTICAL MANUFACTURING

(71) Applicant: Amol S. Matharu, East Windsor, NJ (US)

(72) Inventor: Amol S. Matharu, East Windsor, NJ (US)

(73) Assignee: Amol S. Matharu, East Windsor, NJ (US)

( * ) Notice: Subject to any disclaimer, the term of this patent is extended or adjusted under 35 U.S.C. 154(b) by 465 days.

(21) Appl. No.: 17/286,535

(22) PCT Filed: Oct. 18, 2019

(86) PCT No.: PCT/US2019/056856
§ 371 (c)(1),
(2) Date: Apr. 19, 2021

(87) PCT Pub. No.: WO2020/081888
PCT Pub. Date: Apr. 23, 2020

(65) Prior Publication Data
US 2021/0386623 A1    Dec. 16, 2021

Related U.S. Application Data

(60) Provisional application No. 62/747,866, filed on Oct. 19, 2018.

(51) Int. Cl.
*A61J 3/00*         (2006.01)
*A61L 9/14*         (2006.01)
(Continued)

(52) U.S. Cl.
CPC .............. *A61J 3/00* (2013.01); *A61J 1/2003* (2015.05); *A61L 9/14* (2013.01); *B01F 33/836* (2022.01); *B65B 3/003* (2013.01); *B65B 55/12* (2013.01)

(58) Field of Classification Search
CPC ......... A61J 1/30; A61J 1/2003; B01F 33/836; B65B 3/003; B65B 55/12
See application file for complete search history.

(56) References Cited

U.S. PATENT DOCUMENTS 4,587,793 A      5/1986  Brennan et al.
5,511,594 A *    4/1996  Brennan .................... A61J 3/00
                                                          53/425
(Continued)

FOREIGN PATENT DOCUMENTS

WO         2018152320 A1    8/2018

OTHER PUBLICATIONS

United States Patent & Trademark Office, The International Search Report and the Written Opinion issued in corresponding International application No. PCT/US2019/056856, dated Jan. 2, 2020, 9 pp.

*Primary Examiner* — Timothy L Maust
(74) *Attorney, Agent, or Firm* — Taft Stettinius & Hollister LLP; Daniel J. Krieger (57) ABSTRACT

A pharmaceutical mobile machine to produce a sterile dosage pharmaceutical form from non-sterile or sterile ingredients amenable for human dosing and administration, The pharmaceutical machine includes an ingredient combiner module including a mixer to mix active and inactive pharmaceutical ingredients and a transfer conduit to transfer the mixed ingredients from the ingredient combiner module. A final product module is operatively connected to the transfer conduit to receive the mixed ingredients from the ingredient combiner module. The final product module includes filling equipment to fill one or more containers to produce the sterile dosage pharmaceutical form. An environment module includes an air purifying system having an outlet operatively connected to the final product module, (Continued)

wherein the air purifying system provides purified air to the final product module through the outlet.

18 Claims, 6 Drawing Sheets

(51) Int. Cl.
*A61J 1/20* (2006.01)
*B01F 33/80* (2022.01)
*B65B 3/00* (2006.01)
*B65B 55/12* (2006.01)

(56) References Cited

U.S. PATENT DOCUMENTS

2006/0048844 A1 3/2006 Merrill et al.
2016/0008757 A1 1/2016 Gromala et al.

* cited by examiner

PORTABLE APPARATUS AND METHOD FOR STERILE PHARMACEUTICAL MANUFACTURING

CROSS-REFERENCE TO RELATED APPLICATION

This application is a U.S. National Phase application of International PCT Application No. PCT/US2019/056856 filed on Oct. 18, 2019, which claims priority to U.S. Provisional Patent Application Ser. No. 62/747,866, having the title "A Portable Stand-Alone Apparatus and Method for On-demand Pharmaceutical Sterile Manufacturing" filed Oct. 19, 2018, the disclosures, each of which i-s are incorporated herein by reference in its their entirety.

FIELD OF THE DISCLOSURE

The present disclosure relates to an apparatus to manufacture pharmaceutical products, and more particularly to a portable apparatus to manufacture pharmaceutical products on an as-needed basis.

BACKGROUND

Recently, sterile preparations in pharmaceutical and biotechnology industries have experienced increased costs associated with the development of new pharmaceutical products. Additionally, a shortage of several such different types of preparations is prevalent. While individual processes involved in certain pharmaceutical manufacturing are transitioning to continuous-like processes, pharmaceutical facilities generally still rely on batch or semi-batch techniques to produce sterile preparations stored in vials and syringes. Current processes are typically tailored to manufacture a single specific type of product and generally require large, expensive, and static setups. While continuous processes may offer numerous benefits, including reduced cost, complete infrastructure and systems capable of reliably producing a sterile product on a continuous manufacturing platform do not exist. Moreover, a mobile unit capable of producing sterile preparations remains to be developed.

PCT publication WO2018/152320 discloses a modular portable apparatus for tablets, however, a sterile portable apparatus has not been disclosed. A device exists which can perform a compounding operation using sterile ingredients. However, a processing capability to produce sterile finished products from non-sterile ingredients has not been disclosed. The device is known as i.v. Station available from Omnicell, Inc. 590 East Middlefield Road Mountain View, CA 90434.

The stringent nature of the pharmaceutical sterile manufacturing makes it susceptible to manufacturing facility related and supply chain issues. The footprint of such facilities is large with massive running costs. Additionally, the fragile nature of this sector creates unexpected interruptions in supply chain causing frequent shortages which impacts patients directly. These issues are more severe for locations which are remote, require special supply-chain handling and catastrophic events where a sterile drug-product is required on an urgent basis for life saving efforts at the point-of-care. What is needed therefore is a method to process non-sterile ingredients and convert those ingredients into a sterile pharmaceutical composition using a portable transportable pharmaceutical manufacturing system.

SUMMARY

In the present disclosure, a compact, portable, stand-alone, reconfigurable, and automated sterile manufacturing system-is provided. By way of non-limiting example, in one embodiment, the portable system of the current invention includes two or more modules and is roughly the size of a standard refrigerator. Portable systems of various sizes and dimensions are within the scope of the invention, the only requirement being that the system is sized to be portable. A portable apparatus is defined as one which does not require significant disassembly to be moved. It should be noted that the system is a modular system and is capable of being disassembled into individual modular components. This apparatus manufactures on-demand sterile fill-finish dosage form which is ready for administration. This apparatus can accommodate low production capacity up to a high capacity (few to several thousands) based on continuous running principles. The stand-alone system, once set up, is configured to produce products without further human intervention based on a computer program operated by processor. Once the system is fully configured to produce products, the system includes all the necessary materials and devices to produces a final product automatically, uninterrupted and continuously without further human intervention.

The described embodiments process non-sterile ingredients and convert those ingredients into a sterile composition.

In one embodiment, there is provided a method of producing a sterile pharmaceutical composition including the steps of: combining non-sterile or sterile excipient(s) and non-sterile or sterile active pharmaceutical ingredient(s) in a first enclosure; transferring the combined excipient(s) and active pharmaceutical ingredient(s) from the first enclosure to the second enclosure; purifying the air in the second enclosure with a third enclosure operatively connected to the second enclosure; and filling a container in the second enclosure with the combined excipient and active pharmaceutical ingredient to produce the sterile pharmaceutical composition.

In another embodiment, there is provided a pharmaceutical machine to produce a sterile dosage pharmaceutical form amenable for human dosing and administration. The machine includes a first enclosure having a mixer, wherein the mixer combines an excipient and an active pharmaceutical ingredient. A second enclosure is operatively connected to the first enclosure to receive the combined excipient and the active pharmaceutical ingredient, wherein the second enclosure includes filling equipment to fill a container with the received combined excipient and active pharmaceutical ingredient. A third enclosure is operatively connected to the second enclosure through a connector, wherein the second enclosure includes a purifying system to purify air received from the third enclosure through the connector.

In a further embodiment, there is provided a pharmaceutical machine to produce a sterile dosage pharmaceutical form amenable for human dosing and administration. The pharmaceutical machine includes an ingredient combiner module having a mixer to mix active and inactive pharmaceutical ingredients and a transfer conduit to transfer the mixed ingredients from the ingredient combiner module. A final product module is operatively connected to the transfer conduit to receive the mixed ingredients from the ingredient combiner module. The final product module includes filling equipment to fill one or more containers to produce the sterile dosage pharmaceutical form. An environment module includes an air purifying system having an outlet operatively connected to the final product module, wherein the air purifying system provides purified air to the final product module through the outlet.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

DETAILED DESCRIPTION

Systems and methods related to combining solid and liquid excipients, including pharmaceutical sterile preparations, are described as follows.

In the pharmaceutical industry, pharmaceutical sterile preparations are typically made from large batches on the scale of kilos to tons. Consequently, the ability to fabricate pharmaceutical sterile preparations in a portable, self-contained, and/or readily reconfigurable system has not been demonstrated. Such processes require a large investment in equipment, space and materials. Also, with substantial expense tied to each batch, substantial financial losses are associated. Recently, such manufacturing spaces have shown significant quality issues and maintenance issues resulting with batch loss or product discontinuity. For the product to be shipped to remote locations, a longer shelf-life of several years or months may be required. This generally may not be achievable for injectable preparations where stability cannot be achieved requiring a cold-supply chain. Point-of-sale administration does not exist. When shelf-life is of concern, additional supply-chain solutions may be required adding to the costs. As a result, packaging appropriate to sustain a long shelf life is designed and tested.

Described herein is an apparatus and method for making pharmaceutical, sterile dosage forms. The apparatus, which in one embodiment, is a self-contained unit having individual modules, provides various benefits over conventional batch processes and batch apparatus. In some cases, the apparatus provides one or more benefits; for example, (1) help address regional drug shortages, (2) provide a solution for drugs with a short shelf life, (3) be reconfigurable to produce multiple drug products, (4) be located at or transported to locations where drug products are required, (5) be put into immediate production of drugs based on demand, bypassing the need to stockpile drugs, and/or (6) reduce formulation complexity relative to products needing year-long stability.

Producing sterile dosage forms presents additional problems such as maintaining a particulate free atmosphere and sterile equipment amenable to produce high quality dosage forms which are particle and, micro-organism free. Sterile filtration is also required for liquid sterile dosage forms. Sterility assurance and total particle counts are a concern and a reason for failure for commercial sterile manufacturing plants due to their larger footprint, and also due to their age. High maintenance costs and age are some typical reasons as to why firms decide to shut them down as these could lead to quality issues.

According to one aspect of the invention, the portable system is a compact, portable unit. In some embodiments, the portable system holds and processes volumes of material that are smaller, preferably much smaller than those of traditional batch. Consequently, the portable system is used in different embodiments for the production of both small batch or a large batch of fill-finish products. The system is also used for testing the development of products (i.e., in the research and development phase, prior to mass production).

In some embodiments, multiple components of the system are coupled together to a common frame or enclosure, as opposed to having large components independent of one another spread out over a facility floor.

According to one aspect, the method involves using portable system according to the invention to fabricate a first liquid system and a second liquid system, the two liquid systems being different from one another. In some embodiments, the two systems may include the same Active Pharmaceutical Ingredient (API), but be of different dosages. The API is the part of any drug that produces its effects. In some cases, the system may automatically switch between production of the two different systems without any physical changes to the system components. In some embodiments, the first system may include an API that is compositionally different from the API of the second system. Some drugs, such as combination therapies, have multiple active ingredients to treat different symptoms or act in different ways.) and excipient-chemically inactive ingredients) (granular-raw material-particulate-loose-aggregate)

According to one aspect, the sterile preparations are produced on-demand, e.g., a user may input an instruction to the system specifying the desired dosage and/or desired API of the preparation. In some embodiments, a user may specify the number of desired dosage form units. In response, the system dispenses the appropriate type and amount of API and excipient to form a blended liquid mix for the sterile preparation in accordance with the user's instruction. In some embodiments, the system includes a controller that receives the user's instruction and controls the system components to carry out steps in accordance with the instruction. One or more different kinds of excipients are used in different embodiments to arrive at different compositions.

The system comprises a plurality of modules that interact with one another. For example, in certain embodiments, the system comprises multiple modules that interact with one another. In some such embodiments, each of the modules within the system is used to perform one or more steps of a multi-step production process. These steps include not only combining various composition material of the product, but also essentials of sterile dosage form preparation such as sterile filtration and related processes.

According to one aspect, a weighing function and conveying function are integrated into one material carrying module. In some embodiments, a controller controls the operation of the system. The controller receives feedback from one or more modules of the system and/or provides control instructions to one or more modules of the system. In one or more embodiments, the instructions include instruction for the preparation of a plurality of sterile preparations. Production for each of the sterile preparation is selectable through a display.

In one or more embodiments, he API and excipient (solid or liquid) are dispensed and weighed at different times, such that the system determines the mass of each type of dispensed material. For example, the system first dispenses the API and then weighs the dispensed API. The system then subsequently dispenses excipient and then weighs the dispensed excipient. In some embodiments the API dispenses into a solvent or container closure, and the excipient is dispensed into the same container closure holding the dispensed API. The system determines the mass of the excipient based on the increase in weight detected after the excipient was added. In other embodiments, each of the materials is weighed separately.

In some embodiments, after weighing, the API and excipient are conveyed to a mixing tank. In such embodiments, weighing occurs prior to conveying the API and excipient to mixing tank. However, in other embodiments, weighing occurs in the mixing tank itself. In either case, with the API and excipient (solid or liquid) present in the mixing tank, the blender mixes the API and excipient together into a mixed blend or solution or suspension. In different embodiments, the solution is aqueous or non-aqueous. In some embodiments, the mixed liquid is then dispensed into a large bag for direct intravenous administration. In some embodiments, the mixing is conducted in an IV bag. In some embodiments, the mixed liquid is then dispensed into smaller, discrete amounts that are received by a suitable sterile administration unit such as a vial or syringes.

In some embodiments, the system is configured to produce at least about ten (10) to several thousand doses per day. As will be generally understood by one skilled in the art, the term dose generally refers to an amount of an active pharmaceutical ingredient which is administered to an organism (e.g., a person, an animal, a plant, an insect, and/or a bacterium) to stimulate a biological response.

In another embodiment, several apparatuses are joined to produce sterile dosage forms starting from API, which in-turn is made from starting material.

In certain embodiments, the system is configured to produce a relatively high amount of sterile preparations in a small footprint. In one embodiment, the sterile mobile equipment may have analytical capability to detect particulates (in the preparation and enclosed space), assay the drug preparation, and other tests (such as pH and not limited to) required to assure the quality of the product (FIG. 1).

Sterile preparations include but are not limited to vials, IV bags, syringes, tubes, bottles, and the like. In addition, the disclosed systems are used in different embodiments for the preparation of human dosing and administration as well as veterinary dosing and administration.

Non-limiting embodiments of the present invention are described by way of example with reference to the accompanying figures, which are schematic and are not intended to be drawn to scale. In the figures, each identical or nearly identical component illustrated is typically represented by a the same numeral throughout the Figures. For purposes of clarity, not every component is labeled in every figure, nor is every component of each embodiment of the invention shown where illustration is not necessary to allow those of ordinary skill in the art to understand the invention.

Figure 1A:
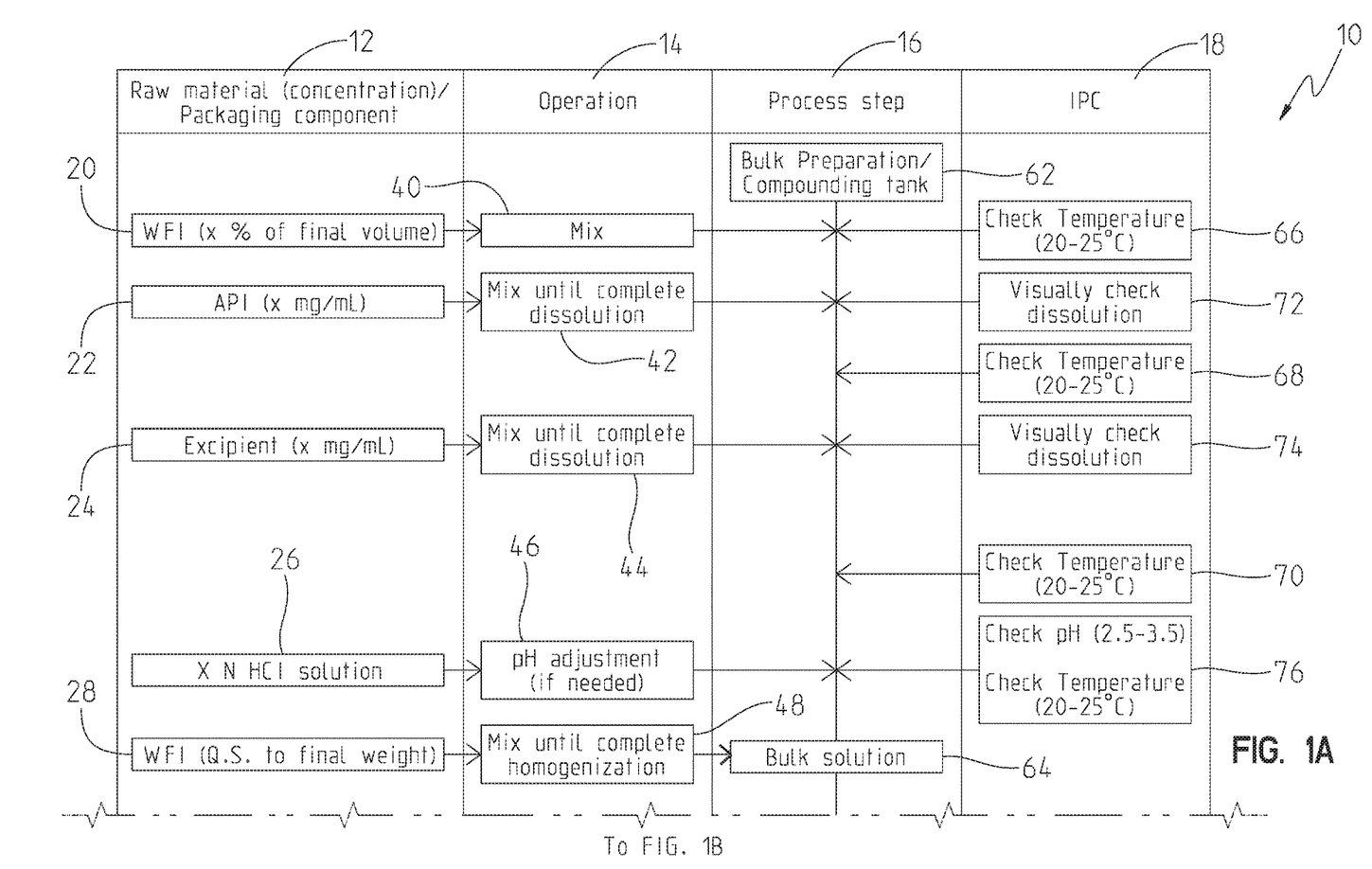
FIG. 1 is a schematic diagram of process steps made by one or more of the disclosed systems for producing sterile pharmaceutical products.
Figure 1B:
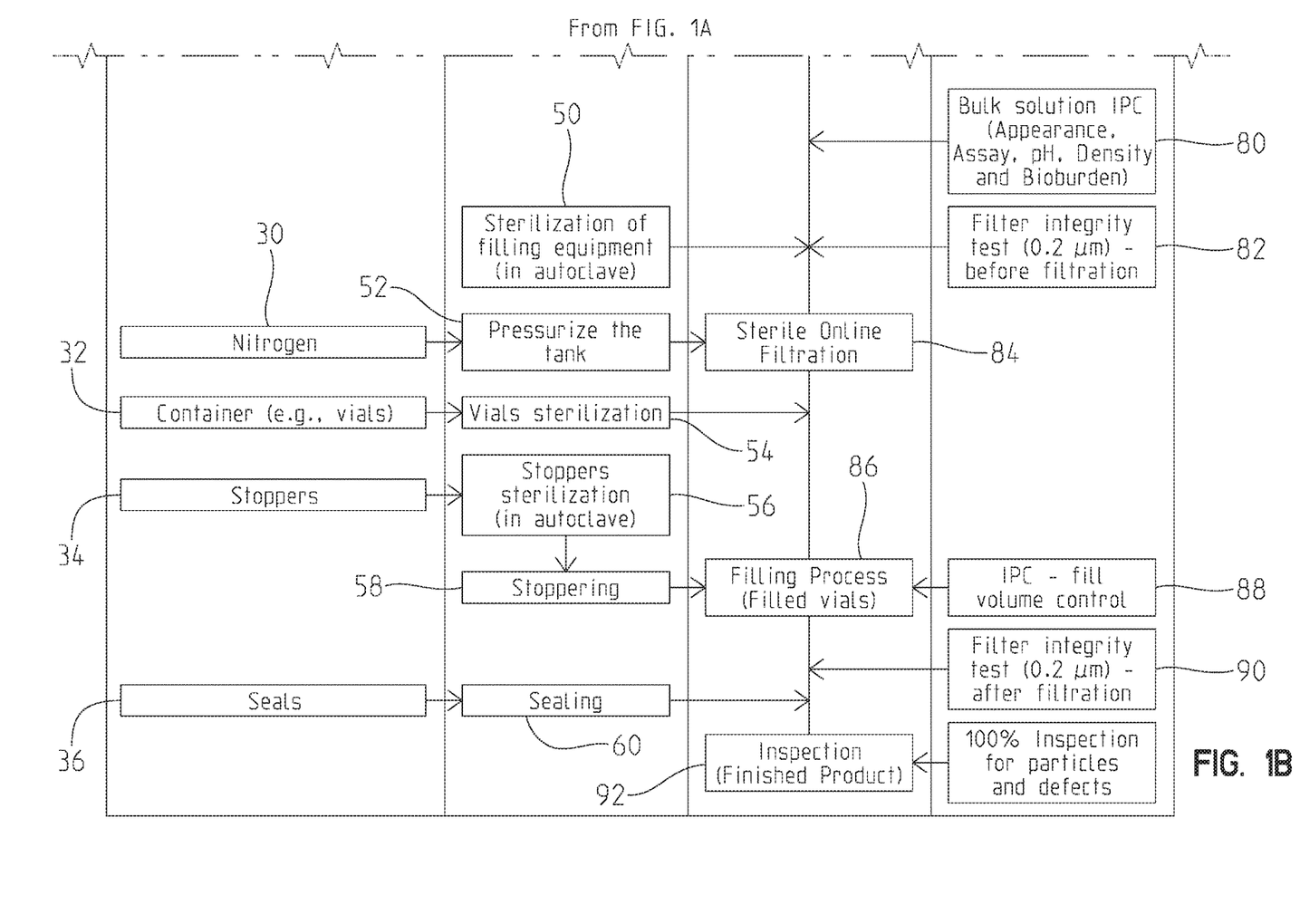

As illustrated in FIG. 1, a process 10 is illustrated for one or more embodiments of a system for producing sterile pharmaceutical products as are illustrated in FIGS. 2-5. Each of the systems include raw material/packaging component processes 12, operation processes 14, a process steps 16, and initial production checks 18. The process 12 includes the use of water for injection (WFI) 20 which is provided as a percentage of the final volume of the of the final products. An active pharmaceutical ingredient (API) 22 is provided as a percentage of the final products as measured by weight or by volume. An excipient 24 is also provided as an inactive substance to provide a medium for the active substances to be used in a final formulation of the product. A hydrogen chloride (HCL) material is provided by weigh and or volume. Additional WFI 28 is provided, if necessary, to achieve a predetermined final weight of the completed formulation.

In addition to the raw materials 20, 22, 24, and 26, packaging components include nitrogen 30, containers 32, and stoppers 34 configured to receive the materials being combined into the final product. Seals 36 are provided to seal the stoppers 34 to the containers 32 for maintaining the sterile nature of the final composition being prepared.

Once each of the material and packaging components have been sourced and are available for use in the process 10, each of the materials provided in process 12 is prepared for use to arrive at a final product. The WFI 20 is mixed at step 40, the AFI is mixed for complete dissolution at step 42, and the excipient 24 is mixed for complete dissolution at step 44. If necessary, the pH of the HCL solution is adjusted at step 46 and additional WFI 28 is added if necessary to insure complete homogenization at step 48. Each of the systems as illustrated in FIGS. 2-5 include filling equipment (to be described later) which are sterilized at step 50.

The functions for each of the packaging components include pressurizing the tank 52 for the nitrogen 30, sterilizing 54 the containers (vials) 32, sterilizing 56 the stoppers 34 for stoppering 58 the containers 32, and sealing 60 the stoppers 34 to the containers 32.

Process step 16 includes the use of a bulk preparation/compounding tank step 62 that includes the use of one or more preparation and/or compounding tanks. Please see containers 120 and 128 described later in FIGS. 2, 3, and 4 as examples. Each of the ingredients, WFI 20, API 22, and HCl 26 is combined to arrive at a bulk solution 64. To arrive at the bulk solution and number of IPC steps 18 are employed to arrive at the bulk solution 64. These steps include checking temperatures of the materials in the preparation/compounding tank 62 at steps 66, 68, and 70. As seen in FIG. 1, each of the check temperature steps 66, 68, and 70 is determined after or during one of the operations steps 40, 42, and 44. In addition, visual checks 72 and 74 are made to determine the dissolution of the mixed materials at mix step 40 and mix step 42. The visual checks 72 and 74 are made by a user making a visual observation of the mixed materials or by a camera system that displays visual information on a display screen to a user, or by an image processing algorithm programmed to determine the state of the dissolution through manufacturing video/data analysis that provides an indicator of proper mixing. The pH level and temperature of the mixed materials are determined at steps 76.

Once the bulk solution is complete at step 64 and has passed each of the checks made at steps 66, 68, 70, 72, 74, and 76, the bulk solution IPC is made at step 80 to determine whether the appearance, the assay, the pH level, the density and the bioburden are satisfactory. If so, a filter integrity test is performed at step 82 to determine whether one or more filters located in the modular apparatus is operating correctly before filtration occurs. Once the filter integrity test is performed, the bulk solution is filtered and sterilized at step 84. After step 84, a filling process 86 begins to fill the container with a correct amount of material as determined by a fill volume control feature. Once each of the containers if filled, a filter integrity test 90 is made after filtration to insure that the filtration process was correct during filtration. Lastly, the finished product is inspected at step 92 to determine if each of the containers is acceptable and meets the requirements for lack of particles and minimum defects.

Figure 2:
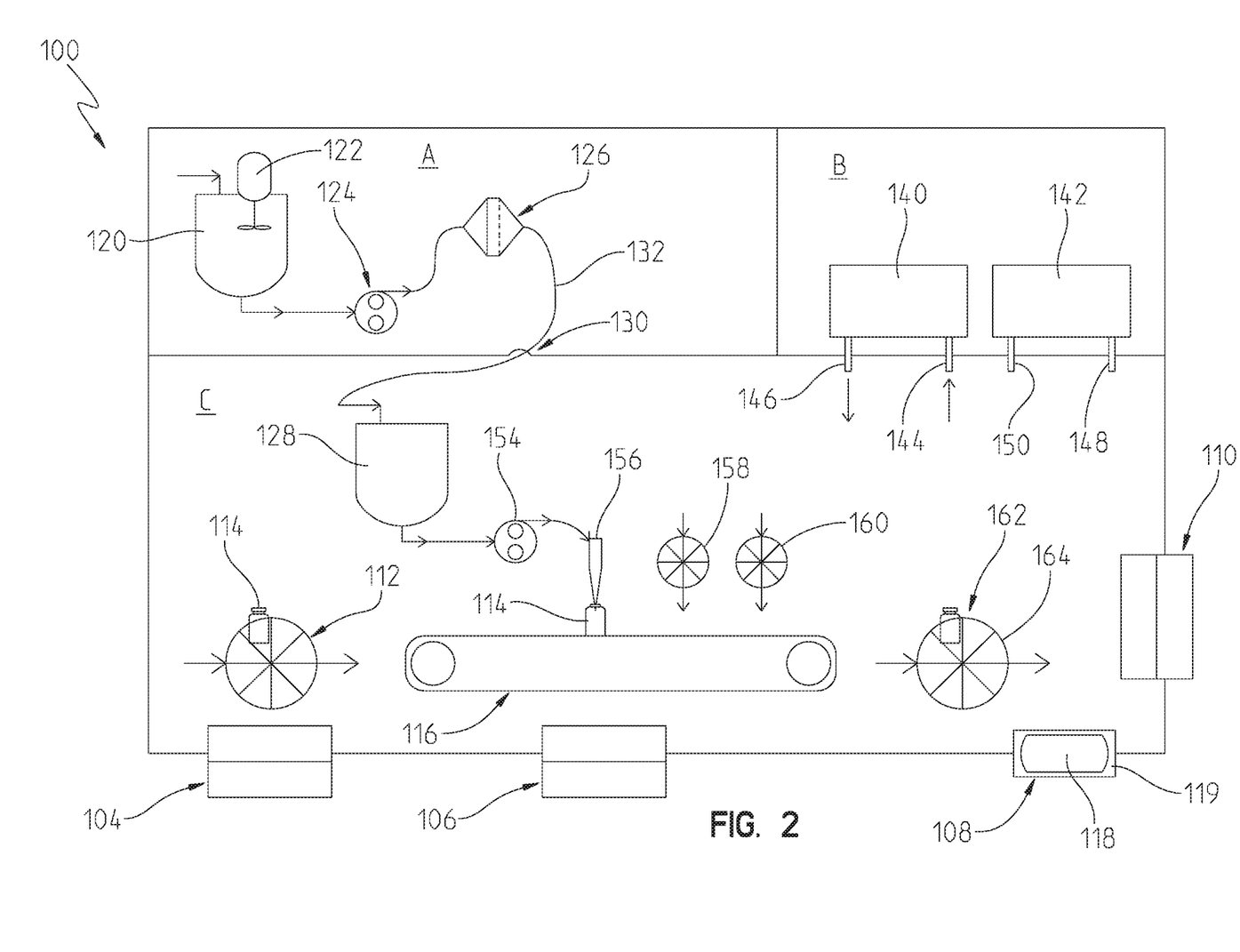
FIG. 2 is a schematic illustration of one embodiment of system for producing sterile pharmaceutical products.

FIG. 2 illustrates a system 100 including an ingredient combiner module A, an environment module B, and a final product module C integrated as a mobile device capable of producing sterile products from non-sterile or sterile ingredients. In one embodiment, each of the modules is housed in the system 100, which may include a housing or enclosure for each of the modules A, B, and C. Each of the modules A, B, and C, in one embodiment, is a self-contained module within an enclosure indicated by the solid black line such that module A and module B are adjacently located to one another and both of the modules A and B are adjacently located to module C. In one embodiment, the modules A and B are stacked side by side on top of module C. In another embodiment, modules A, B, and C are each supported on a surface, such a floor located inside a facility. In another embodiment, each of the modules A, B, and C is located within a larger housing that completely encompasses all of the modules A, B, and C. Such an enclosure maintains the position of each of the modules with respect to one another as well maintains interconnections between modules.

The enclosure for module C, in one embodiment, includes one or more ports 104, 106, and 108, and 110. Each of the ports provides access by a user into or out of module C. Port 104, for instance, provides access to a carousel 112 which carries empty containers 114 to a conveyor system 116 where containers 114 are filled. Port 106 provides access for the user to the conveyor system, if needed, to correct positioning issues of the containers 114. In one embodiment, the conveyor system includes a conveyor belt. In another embodiment, the belt 116 is a robotic system that positions and holds containers 114 for filling. The port 108 provides electronic access through a display 118 which a user utilizes to operate the system 100 which is operated based on a controller 119 through which the display has access. The port 110 provides an access location for delivery of finished product from the module C. Each of the modules is integrated to work together under control of the controller 119.

The controller 119, in different embodiments, includes a computer, computer system, or other programmable devices. In other embodiments, the controller 119 includes one or more processors (e.g. microprocessors), and an associated memory, which can be internal to the processor or external to the processor. The memory can include random access memory (RAM) devices comprising the memory storage of the controller 119, as well as any other types of memory, e.g., cache memories, non-volatile or backup memories, programmable memories, flash memories, and read-only memories. Memory storage, in other embodiments, is located in the "cloud", where the memory is located at a distant location which provides the stored information wirelessly to the controller 119.

The controller 119 executes or otherwise relies upon computer software applications, components, programs, objects, modules, or data structures, etc. Software routines resident in the included memory operatively connected to the processor, or other memory, are executed in to control the operations of one or more of the modules including modules A, B, and C.

Module A receives the ingredients which are mixed in a container or holding tank 120 using a mixer 122. The ingredients being mixed in holding tank 120 include one of or both of excipients and APIs. In one or more embodiments, module A includes a plurality of mixers 122. In different embodiments, the container 120 additionally includes a weigh scale. The material being mixed is transferred by a pump 124 to a filter 126 which filters the mixed material to remove unwanted materials or contaminants. The filtered mixed material is moved from the filter 126 to a holding tank 128 located in module C. The holding tank 128 receives a completed composition or combination of excipient and API. The completed composition results from combining sterile or non-sterile excipients and sterile or non-sterile APIs. In one embodiment, a weigh scale determines the weight of material in the holding tank. A connector 130 is located at an interface between adjacent surfaces of module A and module C. The connector 130 includes in one embodiment aligned apertures of module A and module C through which a transfer conduit is located to move the filtered mixed material to the holding tank 128. In another embodiment, the connector 130 is a male/female connector connecting individual conduits which meet at the interface 130. The interface is configured to align adjacent surfaces of modules at predetermined locations to enable connection of conduits, tubes, and connectors and as well as to align modules in a transportable unitary device. Other connectors are contemplated and include tubes, ducts, and electrical wires. In one embodiment, module A is an ISO 7 or ISO 8 volume. In other embodiments, each of the modules includes interlocking connectors that align with connectors of an adjacent module.

Because the system 100 is modular, the modules are interchangeable. In one embodiment, a first module A includes a first type of API and/or excipient. A second module A includes a second type of API and/or excipient. Because the modules is interchangeable and have different materials, the system 100 is configurable to produce different types of pharmaceutical products with minor modifications to the system 100. Each of the modules is individually replaceable which provides reduced downtime for the overall system. If one module requires maintenance or repair, that module is replaceable with another module and the system is back in operation without needing to wait on the repair or maintenance of the module being worked on.

Module B includes an air-purifying system 140 and sterility rendering system 142. The air-purifying system 140 is operatively connected to module C purify the air within module C. Module B reduces particulate counts in module C to establish module C as an ISO 5 area, amenable for producing pharmaceutical products such as injectables. Module C is maintained as an ISO 5 area during the manufacturing operation. Sterility rending system 142 sprays agents such as hydrogen peroxide into various locations of module C to render and maintain sterility. As can be seen air purifying system 140 removes air from module C at inlet 144 and delivers purified air to module C at outlet 146. Likewise, sterility rendering system includes an outlet 148 to provide sterility agents to module C and to remove sterility agents at inlet 150 from module C, if necessary, such as airborne sterility agents.

The material or materials are introduced into Module A using transfer devices, such as cassettes, that transfer material into blender mixer 122. In one or more embodiments, the material is a solid or a liquid. The pump 124 transfers liquid from mixer 122 to a filter assembly 126 to facilitate sterility by filtration. This filter assembly 126, in different embodiments, includes a series of filter including a 40 micon filter. Additionally, module A includes a device to measure a bubble point of the filter, which records measurement using the controller 119 the status of which is viewed at the display 118. The filtered solution is transferred to the holding tank 128 in module C. In one embodiment, the holding tank is configured to hold a final preparation having a volume of up to 100 Liters. Other volumes are contemplated.

The filtered solution is then filled into containers 114 which are fed by the carousel 112 to the belt 116. The filtered solution is delivered by a pump 154 to a solution donator 156, such as a metering device, which in turn directs the solution to each of the containers. A stopper or capping carousel 158 is loaded with stoppers 34, or caps, which are used to close the containers 114 after being filled with the solution. A carousel 160 is loaded with seals 36 which are used to seal the stopper 34 to a respective container 114. Once the containers 114 are closed and sealed, the finished containers are moved a staging area 162, which in one embodiment includes a carousel 164. While carousels are described for moving packaging components from one location to another location, other types of devices are contemplated to move the containers 114, the stoppers 34, and the seals 36 to complete a finalized product.

In some embodiments, the controller 119 controls the operation of the system 100. The controller 119 receives signals from one or more modules A, B, and C of the system 100 which provides status information of each of the modules A, B, and C. For instance in one embodiment, material flow through the conduit 132 is identified by a flow sensor and provide to the controller 119. Likewise, the status of air purification being conducted at module B by air-purifying system 140 is also monitored in some embodiments by a sensor transmitting air purification status information to the controller 119. In another embodiment, metering device 156 of module C provides status signals identifying the amount of material being metered. In one or more embodiments, the status information is used by the controller 119 to modify the operating conditions of the components being monitored. For instance, the flow status signal of material flow through the conduit 132 is used by the controller to determine whether the flow of material being provided by the pump 124 should be adjusted. Consequently, the controller 119, in different embodiments, is configured communicate with and to provide control instructions to one or more modules and the components of modules. In some embodiments, the components of each of the modules of the system (e.g., the dispensers, the blender, the carriage, etc.) communicate with one another, with and/or independently of the controller.

While one controller 119 is illustrated, in other embodiments, additional controllers are included in one or more of the modules. In other embodiments, the controller 119 provides for the operation of each of the modules, but does not provides control signals in response to stratus signals received from those modules. In these embodiments, the status signals are displayed on the display 118 to provide status information to a user. In additional embodiments, the controller 119 generates a warning signal for display on the display to notify to the user that a fault condition has occurred.

Figure 3:
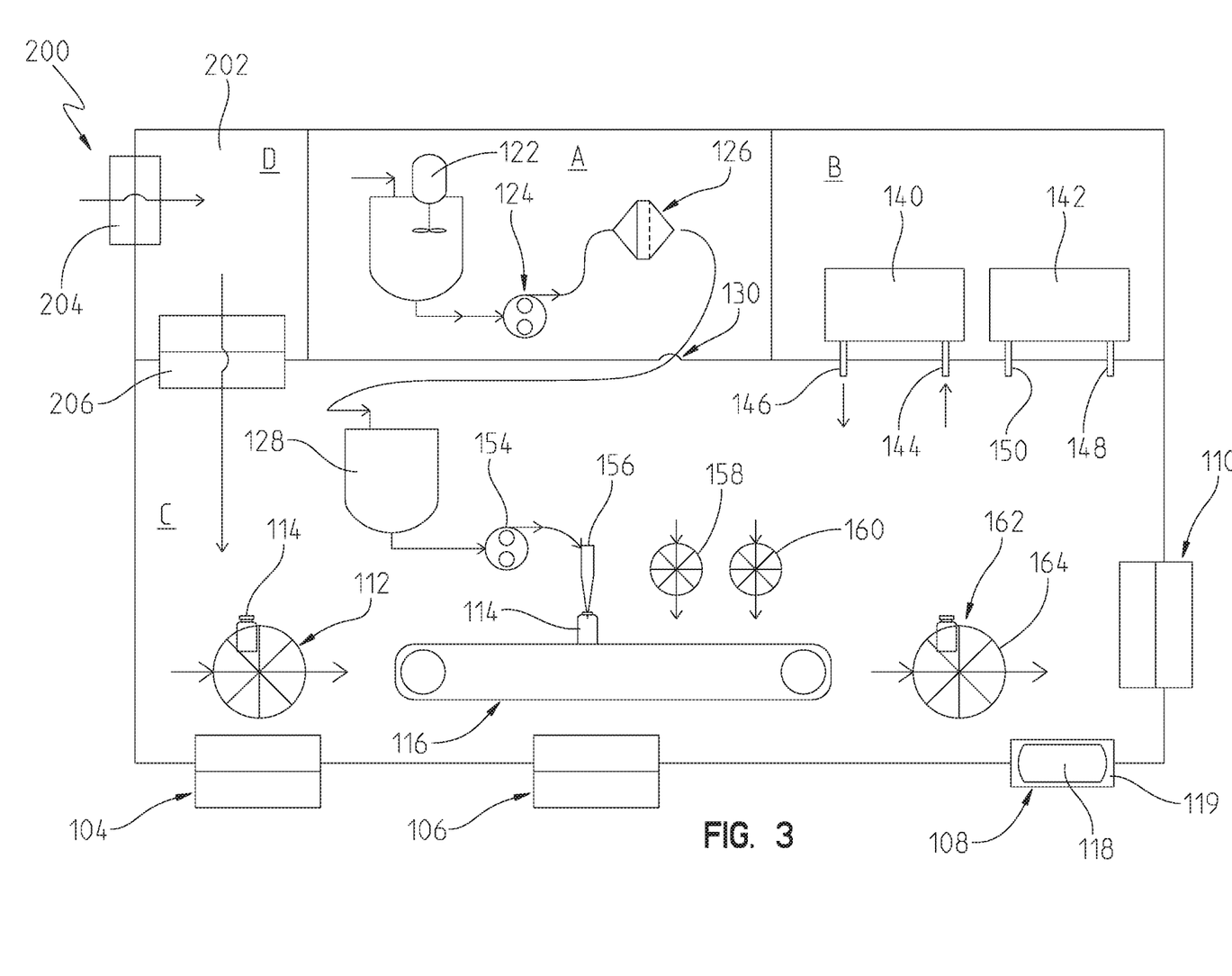
FIG. 3 is a schematic illustration of one embodiment of system for producing sterile pharmaceutical products.

FIG. 3 illustrates a system 200 including the modules A, B, and C of FIG. 2, and further including a module D. In this embodiment, module D includes a washing/depyrogenation system 202 and cooperates with the functions of modules A, B, and C of FIG. 2. The washing/depyrogenation system 202, in different embodiments is optionally added for module C, the final product module to provide clean containers, vials, stopper, caps, and other material for the container closure system. Module D includes ports 204 and 206 to enable material transfer into and out of module D. Production parts for enclosing pharmaceutical materials are introduced into port 204, cleaned, and then the cleans part are moved into module C through the port 206 to provide sterile production.

Figure 4:
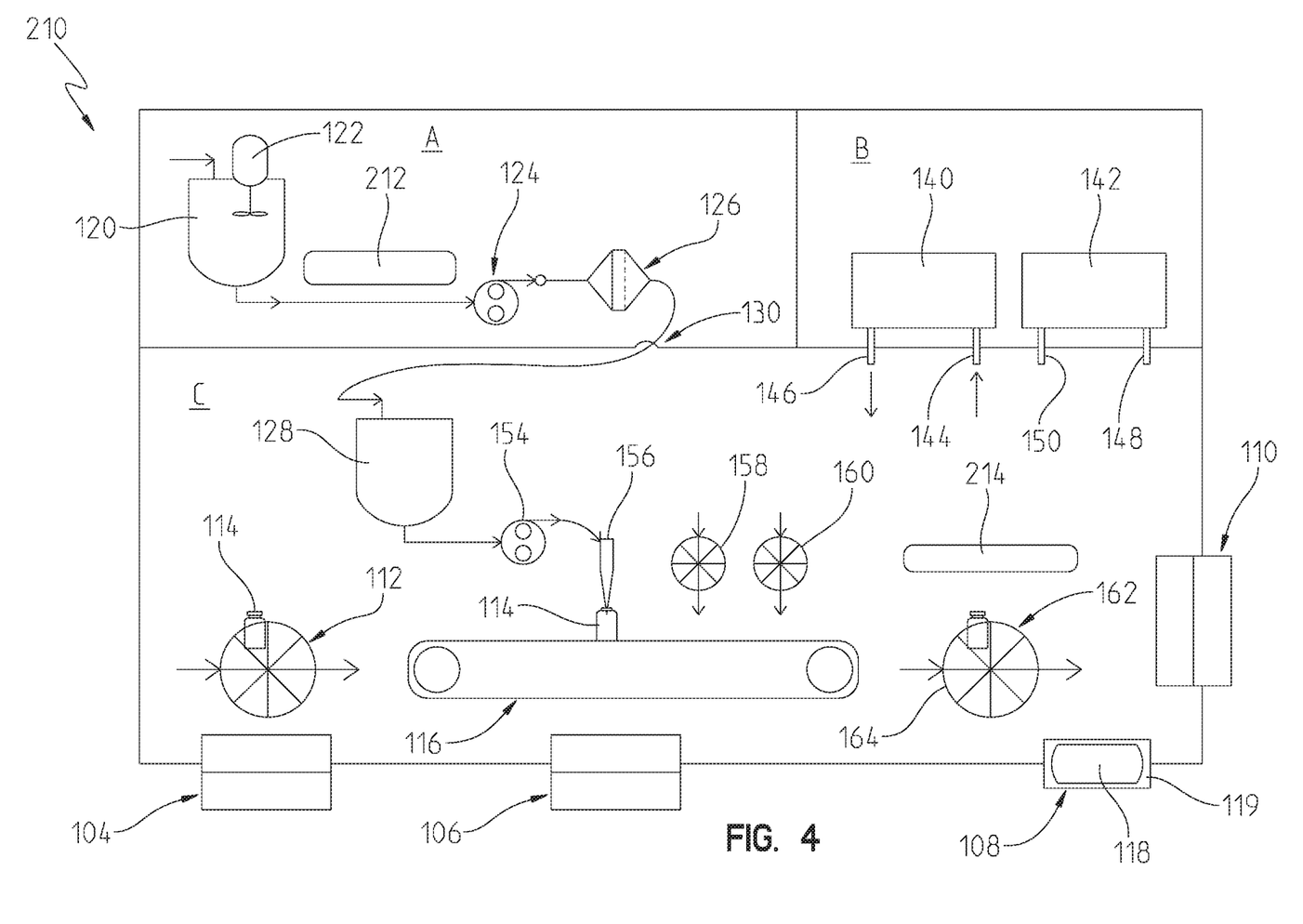
FIG. 4 is a schematic illustration of one embodiment of system for producing sterile pharmaceutical products.

FIG. 4 illustrates a system 210 including modules A, B, and C in which modules A and C have been modified. In this system, module A includes an irradiation device 212 and module C includes an irradiation device 214. Each of the irradiation devices 212 and 214 provide a sterilization system that is optionally added for the incoming material or solutions produced in module A and for the container closure system such as vials, stopper and caps in module C. In one embodiment, the irradiation devices 212 and 214 are gamma-irradiation devices. Other types of irradiation devices are contemplated.

Figure 5:
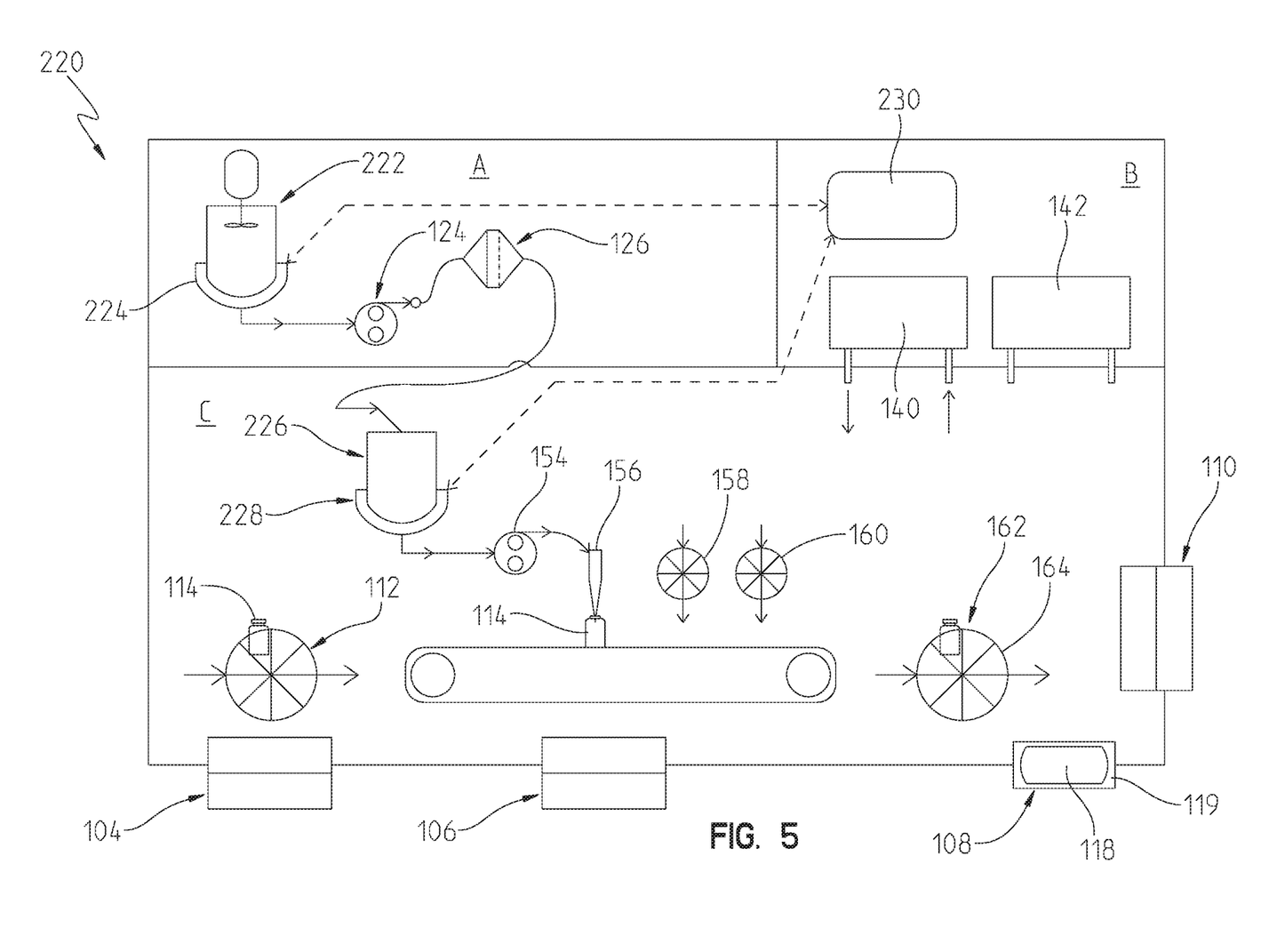
FIG. 5 is a schematic illustration of one embodiment of system for producing sterile pharmaceutical products

FIG. 5 shows an illustrative embodiment of a system 220 including modules A, B, and C in which each of the modules A, B, and C have been modified for use with the mobile sterile production of pharmaceuticals. A jacketed mixer 222 is located in module A and incudes a jacket 224 configured to maintain a temperature of the ingredients being mixed by the mixer 222. A mixer 226 located in module C includes a jacket 228 configured to maintain a temperature of the ingredients being mixed by the mixer 226. Each of the jackets 224 and 228 have temperatures controlled by with a temperature control system 230 located in module B. Each of the jackets 224 and 228 is added to the mixer 224 and/or the mixer 226 to aid in the manufacturing of those ingredients which require a predetermined temperature, either heating or cooling, to aid in stability of the product. The temperature control system 230 is operatively connected to the each of the jackets 224 and 228 as indicated by a dashed line. In one embodiment, the dashed lines indicate electrical connections between the system 230 and the jackets 224 and 228. Each of the jackets includes a temperature sensor configured to transmit a sensed temperature of the associated jacket. The control system 230 in response to the sensed temperature signal adjusts the temperature of the materials through a heater located at the jackets.

Each of the systems 100, 200, 210 and 220 is powered by a power supply which is either part of the systems or is separate from the systems. Power supplies include but are not limited to facility power delivered to the systems by a power outlet, rechargeable battery power, solar, power, wind power, water power, or a combination thereof.

In another embodiment, all the options provided above and not limited to, may be included in a single system, which is mobile. A mobile system may be refrigerator size such that it can be easily moved and placed in remote non-sterile locations to produced sterile parenteral products. Optionally, the mobile system may be transported by vehicles such as a truck, train, boat, or plane in which the described components and arrangements are permanently placed in the vehicle.

In other configurations, each of the modules when combined is configured to be equal to the length, depth, and height of a standard refrigerator. While a refrigerator is used in this example, a refrigerator sized assembly is meant to indicate that the described systems are capable of being moved from one location to the another location in the same sense as a refrigerator is moved by one or two men without the use of moving equipment. In other embodiments, one or more of modules includes wheels to facilitate moving. In some embodiments, a complete system is moved as a single unit with dollies, carts, or hand trucks for maneuvering through the doors of a facility. In other examples, each of the modules is sized similar to a refrigerator, but the final combination of modules is larger than a refrigerator. Because the complete system is made of discrete modules, moving of the system from location to location is optimized and is particularly suitable for reduced scale manufacturing at locations needing immediate production of pharmaceuticals, for instance in remote locations or locations where a natural disaster has occurred or in other emergency situations. In one example, the unitary modular system is sized as standard size refrigerator having a width of 30 to 36 inches, a height of 67 to 70 inches, and a depth of 29-35 inches.

While this disclosure has been described with respect to at least one embodiment, the present disclosure can be further modified within the spirit and scope of this disclosure. This application is therefore intended to cover any variations, uses, or adaptations of the disclosure using its general principles. For instance, the stand-alone machine is also used in the compounding industry as well as for home production of doctor prescribed chronic use drugs. Further, this application is intended to cover such departures from the present disclosure as come within known or customary practice in the art to which this disclosure pertains and which fall within the limits of the appended claims.

What is claimed is:

1. A mobile pharmaceutical manufacturing machine to process ingredients to produce a final product of a sterile pharmaceutical composition, the machine comprising:
   one or more transfer devices, in form of a cartridge or a cassette, wherein each of the one or more transfer devices includes at least one of a non-sterile ingredient or a sterile ingredient;
   a metering device which is connected to the transfer device to allow accurate weighing of the ingredients;
   an ingredient combiner module including a transfer device adapted to receive the one or more transfer devices and to transfer the ingredients from the one or more transfer devices, the ingredient combiner module configured to receive the transferred ingredients wherein the ingredient combiner module includes a mixer and a weigh scale to provide a completed composition from the transferred ingredients;
   a final product module operatively connected to the ingredient combiner module to receive the completed composition, the final product module including a fill-finish system to fill one or more containers to produce a dosage pharmaceutical form from the completed composition; and
   a sterilization system configured to sterilize at least one of the non-sterile ingredient, the transferred ingredients, the completed composition, or the dosage pharmaceutical form.

2. The machine of claim 1 wherein the one or more transfer devices includes one or more cassettes and the ingredient combiner module, the final product module comprise a self-contained single unit to be transported as a single unitary device.

3. The machine of claim 1 wherein the final product module includes a weigh scale to weigh the completed composition.

4. The machine of claim 1 wherein the at least one of the non-sterile ingredient and the sterile ingredient includes a sterile excipient and a non-sterile or sterile active pharmaceutical ingredient.

5. The machine of claim 1 wherein one of the ingredient combiner module or the final product module includes a filter assembly to filter the completed composition.

6. The machine of claim 1 wherein the fill-finish system of the final product module includes a pump coupled to a metering device to provide a metered completed composition to the one or more containers.

7. The machine of claim 6 wherein the fill-finish includes a robotic system that positions and holds the one or more containers as the metering device provides the metered completed composition to the one or more containers.

8. The machine of claim 1 further comprising a capping carousel to close the one or more containers having the metered completed composition.

9. The machine of claim 1 further comprising a user display operatively connected to the ingredient combiner module or to the final product module for a user to operate the machine.

10. The machine of claim 9 further comprising a controller operatively connected to the user display, wherein each of the modules is integrated to work together under control of the controller.

11. The machine of claim 1 further comprising interlocking connectors located at the ingredient combiner module and the final product module to enable an alignment of a transfer conduit with the ingredient combiner module and the final product module.

12. The machine of claim 1 wherein the ingredient combiner module is a first discrete module, and the final product module is a second discrete module, wherein the first and second discrete modules are configurable as a self-contained single unit.

13. A method of producing, on-demand, a plurality of sterile fill-finish dosage form units ready for administration, the method comprising:
   receiving from a one or more cassettes at least one of a non-sterile ingredient or a sterile ingredient;
   transferring, from the one or more cassettes, the at least one of a non-sterile ingredient or a sterile ingredient to an ingredient combiner module;
   mixing and weighing the transferred ingredients in the ingredient combiner module to provide a completed composition;
   transferring, from ingredient combiner module, the completed composition to a final product module;
   filling each of plurality of containers with a dosage pharmaceutical form provided by a dispensing system located in the final product module; and
   sterilizing at least one of the non-sterile ingredient, the transferred ingredients, the completed composition, or the dosage pharmaceutical form.

14. The method of claim 13 further comprising:
   metering the completed composition into each of the plurality of containers with a metering device located in the final product module.

15. The method of claim 14 further comprising:
   capping each of the filled plurality of containers to provide the plurality of sterile fill-finish dosage form units.

16. The method of claim 15 further comprising:
   positioning and holding each of the plurality of containers in a carousel located in the in the final product module as the metering device provides the metered completed composition.

17. The method of claim 16 further comprising:
   receiving at a user display operatively connected to the final product module a number of desired dosage form units to be produced.

18. The method of claim 17 further comprising:
   receiving at a user display operatively connected to the final product module a desired dosage of completed composition to be provided by the final product module.

* * * * *